(12) United States Patent
Linke

(10) Patent No.: US 9,125,696 B2
(45) Date of Patent: Sep. 8, 2015

(54) OSTEOSYNTHETIC DEVICE

(75) Inventor: Berend Linke, Hamburg (DE)

(73) Assignee: DePuy Synthes Products, Inc., Raynham, MA (US)

(*) Notice: Subject to any disclaimer, the term of this patent is extended or adjusted under 35 U.S.C. 154(b) by 1456 days.

(21) Appl. No.: 12/063,836

(22) PCT Filed: Aug. 15, 2005

(86) PCT No.: PCT/CH2005/000471
§ 371 (c)(1),
(2), (4) Date: Sep. 13, 2010

(87) PCT Pub. No.: WO2007/019710
PCT Pub. Date: Feb. 22, 2007

(65) Prior Publication Data
US 2010/0331895 A1 Dec. 30, 2010

(51) Int. Cl.
*A61B 17/86* (2006.01)
*A61B 17/74* (2006.01)
*A61B 17/84* (2006.01)

(52) U.S. Cl.
CPC ............... *A61B 17/74* (2013.01); *A61B 17/86* (2013.01); *A61B 17/844* (2013.01); *A61B 17/864* (2013.01); *A61B 17/8665* (2013.01); *A61B 17/8685* (2013.01); *A61B 2017/8655* (2013.01)

(58) Field of Classification Search
CPC .. A61B 17/86; A61B 17/8605; A61B 17/861; A61B 17/8625; A61B 17/8635; A61B 17/864; A61B 17/8645; A61B 17/8665; A61B 17/8685; A61B 2017/8655; A61B 2017/867; A61B 2017/8675; Y10S 411/922; F16B 35/04; F16B 35/041; F16B 35/06; F16B 25/10; F16B 25/103; F16B 25/106; F16B 25/0084; F16B 25/0089; F16B 25/0094

USPC ........... 606/304, 254, 257–260, 301, 302, 606/308–312, 314, 315, 319, 320, 322, 323, 606/326–329, 246, 65–68, 267; 411/386–387.8, 383, 439, 446, 487, 411/488; 254/100, 103
See application file for complete search history.

(56) References Cited

U.S. PATENT DOCUMENTS 3,530,854 A * 9/1970 Kearney .......................... 606/67
4,657,001 A 4/1987 Fixel ............................... 128/92

(Continued)

FOREIGN PATENT DOCUMENTS

JP 11188044 7/1999
WO WO 97/15246 5/1997

OTHER PUBLICATIONS

International Search Report for PCT/CH2005/000471 dated Apr. 11, 2006.

*Primary Examiner* — Michael T Schaper
*Assistant Examiner* — Tracy Kamikawa
(74) *Attorney, Agent, or Firm* — Baker & Hostetler LLP

(57) ABSTRACT

The osteosynthetic device for the fixation of a bone or bone fragments has a longitudinal axis (6) and comprises a bone screw (1) with a shaft (2) bearing a thread (3), a front end (4) and a rear end (5), said thread (3) having a maximum outer diameter d; and a wing-like blade (7) with a leading end (8) being connected to the front end (4) of the bone screw (1) and a trailing end (9) being connected to the rear end (5) of the bone screw (1). The blade (7) is further provided with a coaxial longitudinal aperture (17) having a length I extending between the leading end (8) and the trailing end (9) and a width w≥d. Further the blade (7) is coaxially and rotatably mounted on said shaft (3) of said bone screw (1).

13 Claims, 2 Drawing Sheets

(56) References Cited

U.S. PATENT DOCUMENTS

| | | | | |
|---|---|---|---|---|
| 4,978,349 A | * | 12/1990 | Frigg | 606/67 |
| 5,300,074 A | | 4/1994 | Frigg | 128/67 |
| 5,741,256 A | | 4/1998 | Bresina | 606/62 |
| 6,159,245 A | * | 12/2000 | Meriwether et al. | 623/17.11 |
| 6,187,007 B1 | | 2/2001 | Frigg et al. | 606/72 |
| 6,193,721 B1 | * | 2/2001 | Michelson | 606/70 |
| 6,409,730 B1 | | 6/2002 | Green et al. | 606/72 |
| 6,921,403 B2 | * | 7/2005 | Cragg et al. | 606/86 R |
| 2002/0045900 A1 | | 4/2002 | Harder et al. | 606/65 |
| 2004/0068258 A1 | * | 4/2004 | Schlapfer et al. | 606/61 |
| 2005/0165402 A1 | * | 7/2005 | Taras | 606/72 |

\* cited by examiner

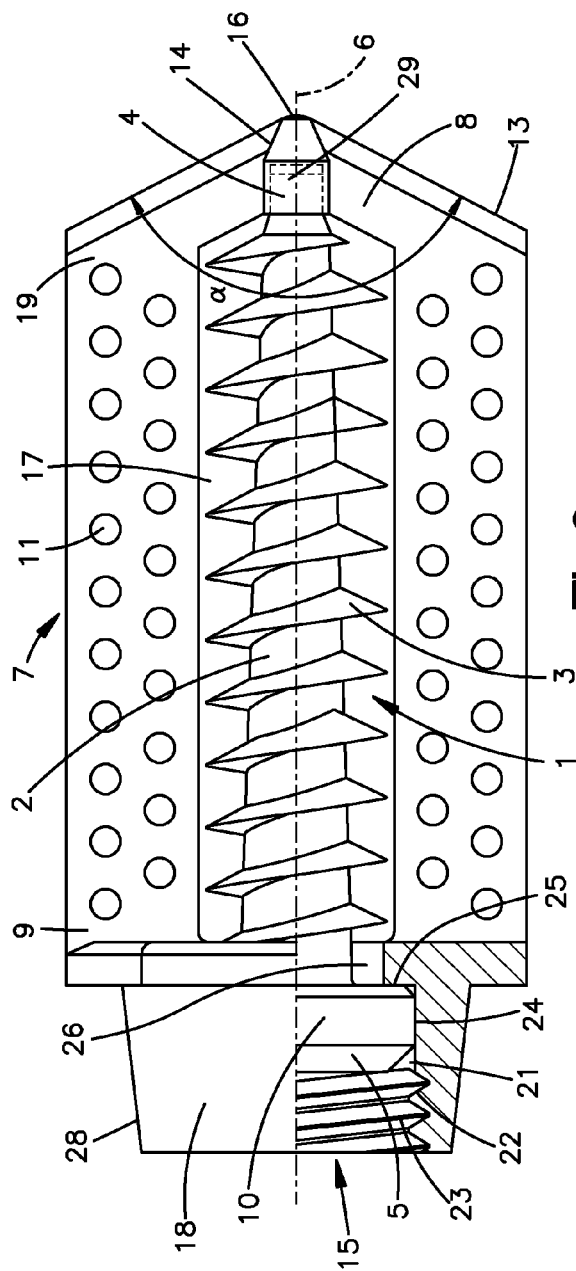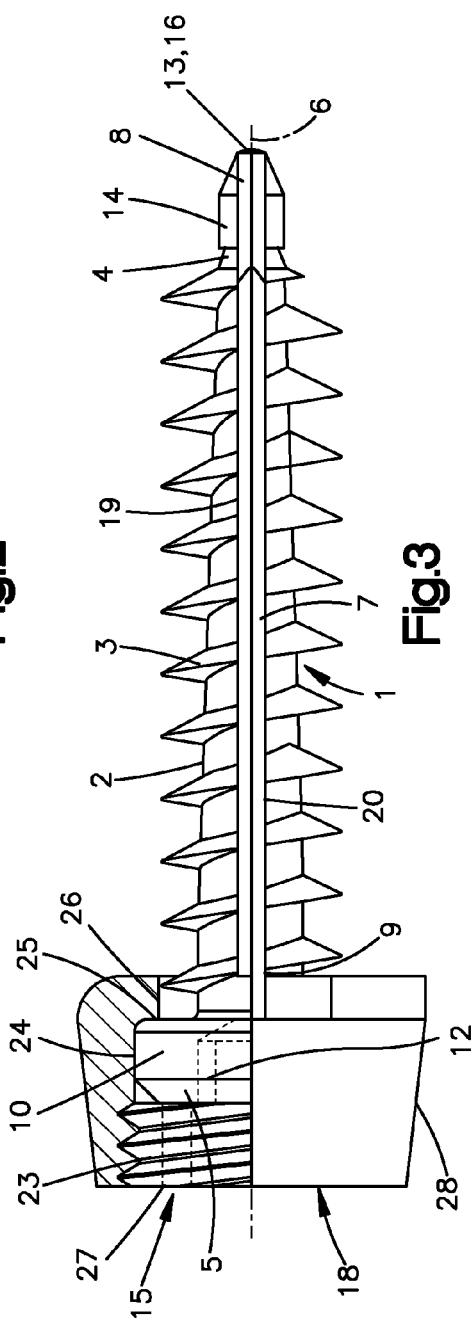

OSTEOSYNTHETIC DEVICE

CROSS-REFERENCE TO RELATED APPLICATIONS

This is a national stage application under 35 U.S.C. §371 based on International Application No. PCT/CH2005/000471, entitled Osteosynthetic Device, filed Aug. 15, 2005, the entire disclosure of which is herein incorporated by reference for all purposes.

FIELD OF THE INVENTION

The invention relates to an osteosynthetic device, and in particular to an osteosynthetic, i.e. a fixation device, for fracture fixation in osteoporotic bone. The osteosynthetic device may be used for all areas of the human skeleton that are predominantly composed of cancellous bone, in particular for the vertebrae and all metaphyseal areas of long bones.

BACKGROUND OF THE INVENTION

From document WO97/15246 an intervertebral implant is known which consists of a screw and a cage rotatably connected to each other. This implant is designed to be introduced between two vertebrae and not as bone screw. The dimensionally large cage—having the function to fill intervertebral space which has to be prepared to this effect—would not be suitable for other applications and is limited to this specific purpose.

SUMMARY OF THE INVENTION

In an embodiment of the invention, the osteosynthetic device may include a bone screw with a shaft bearing a thread, a front end, and a rear end, said thread having a maximum outer diameter d; and a wing like blade with a leading end being connected to the front end of the bone screw and a trailing end being connected to the rear end of the bone screw and said blade further being provided with a coaxial longitudinal aperture having a length I extending between the leading end and the trailing end and width greater than or equal to d, wherein said blade is coaxially and rotatably mounted on said shaft of said bone screw.

BRIEF DESCRIPTION OF THE DRAWINGS

Further objects and advantages of the invention will become apparent from the following description when read with reference to the accompanying drawings which illustrate a preferred embodiment of the invention. In the drawings:

FIG. 2 is a top view on the osteosynthetic device according to FIG. 1; and FIG. 3 is a lateral view on the osteosynthetic device according to FIGS. 1 and 2.

DETAILED DESCRIPTION OF THE INVENTION

Figure 1:
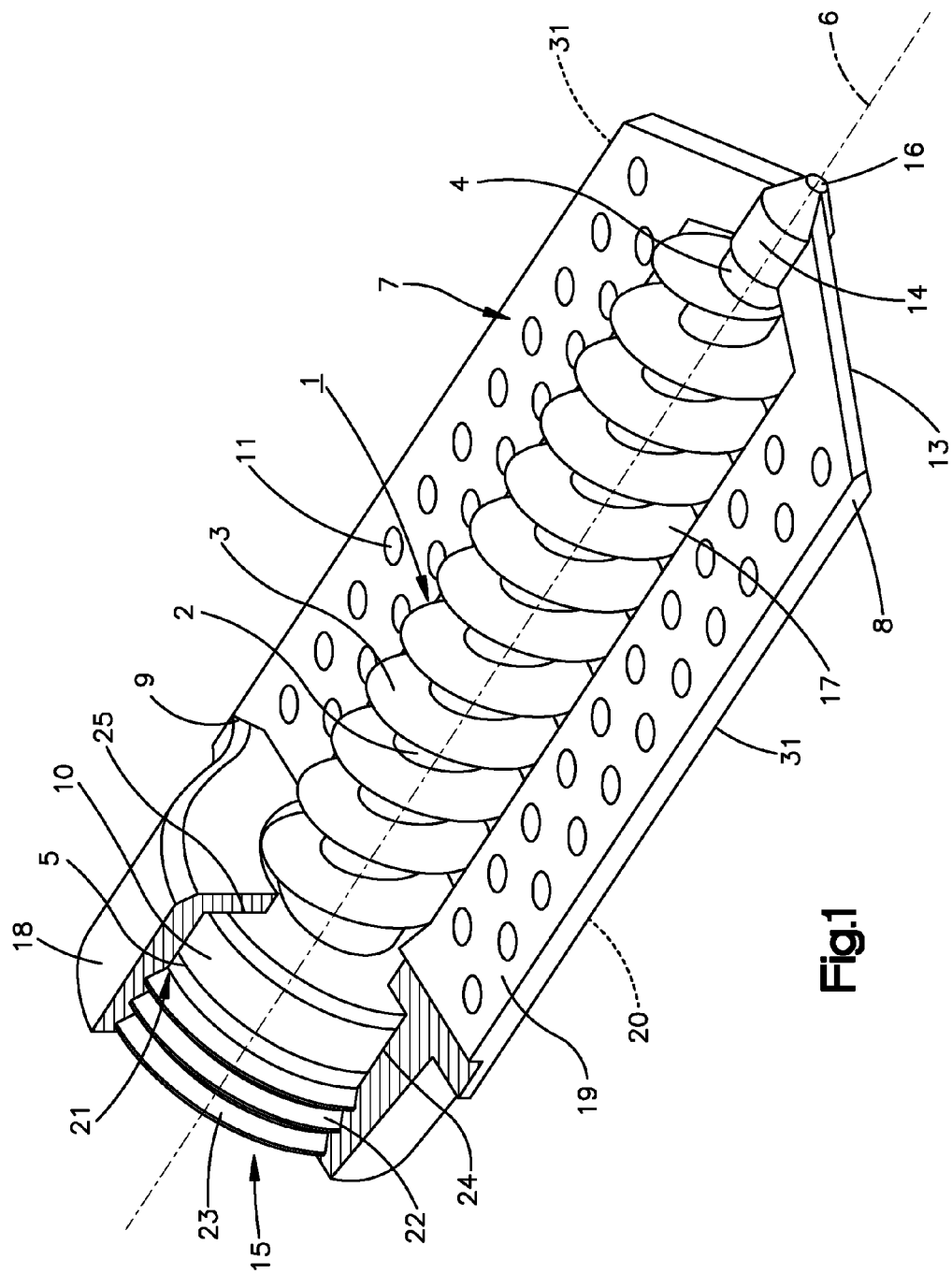
FIG. 1 is a perspective view of an embodiment of the osteosynthetic device according to the invention.

An embodiment of the invention is based on the objective of providing: a) an improved screw type device that has a load bearing function perpendicular to the long axis of the bone screw by improved resistance against loads in this direction; and b) an improved blade type device allowing an improved insertion procedure, which is possible without hammering, and by improved resistance against loads acting along the long axis of the blade, e.g. in intra-operative reduction maneuvers.

The osteosynthetic device according to an embodiment of the invention and illustrated in FIGS. 1, 2 and 3 and further discussed below, combines the main functions of a typical bone screw type device and an osteosynthetical blade type device and thus provides improved anchorage strength against loads from multiple directions (typical in-vivo situation) as compared to both of these devices.

The "wing-like" blade can rotate around the "screw" or vice versa the screw can turn inside the wing during the introduction of the implant and—according to the needs of the particular application—may be secured (blocked) rotationally to each other at the end of the introduction procedure. The rotational blocking can be achieved in an embodiment, for example, by pressing the head of the bone screw against a shoulder by means of a fastener.

For an application aiming at stabilizing a fracture in the neck of the proximal femur and where the wing-like blade is bridging the fracture line, no securing of the rotation is necessary. For other applications—as in the spine area—where no fractures are to be bridged, the rotatability between the screw and the blade is blocked after the insertion in order to obtain a structurally stable implant.

The wing provides improved load bearing capacity against loads acting perpendicular to the long axis of the screw—compared to a normal screw—due to its comparatively large surface area and thus reducing the risk of "cutting out" of the implant through cancellous bone.

The wing also provides rotational strength against loads around the long axis after it is blocked to the screw at the end of the insertion. Both of these features are of special importance when fractures in osteoporotic bone condition are to be stabilized.

The screw provides improved pullout resistance against loads acting along the axis of the screw—compared to blade type devices. The screw also prohibits a "cutting through" of the wing along the long axis, as it is rigidly connected to the wing.

Some of the advantages of the osteosynthetic device according to an embodiment of the invention can include, but or not limited to one or more of the following:

1. Combination of the main screw function (e.g. resistance against pullout/loads acting in line with its long axis) and the main blade function (e.g. resistance against subsidence/loads acting perpendicular to its long axis) in one device that is as easy to implant as a screw and as easy or better to implant than a blade. This leads to improved anchorage of the device compared to screws and compared to blades in their respective "weak" directions.
2. Possibility of introduction without hammering and thus reducing the risk of losing the reduction during this procedure due to the applied high impact forces.
3. Possibility of introduction without an aiming arm that assures the necessary twist for the introduction of normal helical blade type devices.
4. Possibility of hammering in the wing-like blade first and then securing it with the bone screw afterwards is also given, according to the surgeons preference.
5. In summary the osteosynthetic device provides all the advantages of a blade type device with respect to subsidence, but allowing an introduction like a normal bone screw without drawbacks.
6. Provision of sufficient anchorage strength in the fracture fragments against all loads in axial, perpendicular (bending) and torsional direction to allow for intra-operative reduction maneuvers with it which typically have to withstand higher loads during the reduction maneuvers than later on during daily activities.

7. The osteosynthetic device can be applied to almost any site of the human skeleton where it is important to withstand loads from various directions in the post operative phase and where the fixation element of the load bearing implant has to find its major anchorage strength in cancellous bone.

8. Manufacturing of the osteosynthetic device is by far less complicated as compared to a hollow bone screw, which is a screw type device with a large surface area.

9. The osteosynthetic device can be "tuned" optimally to the normal loading conditions during daily activities (and the loads necessary during reduction). When pullout forces are dominant, the outer diameter of the bone screw is rather large and the wing-like blades may be designed rather small. If the main loads are directed perpendicular to the long axis, the outer diameter of the bone screw may be chosen smaller and the wings of the wing-like blade are wider.

10. Wings with different shapes of their leading and trailing ends can be manufactured with respect to the application side, e.g. for a ventral application in a vertebra the leading end can be made a) rather round for maximum load bearing area in osteoporotic conditions and b) rather sharp for reduced introduction resistance in better bone quality.

11. The wing-like blade can be made as an "add-on" to a screw or even only to the front part of a screw, depending on the necessity of the respective surgical condition, e.g. in the head area of the femur in a stabilization of a proximal femur fracture.

12. The core of the screw and the threads can be kept rather thin, to preserve as much bone as possible, as the load bearing surface perpendicular to the axis of the screw is provided by the wings of the blade.

In an embodiment, blocking means are provided for alternatively blocking or de-blocking the rotation between the blade and the bone screw. The blade may be rotatively and axially blocked relative to the bone screw in order to obtain a structurally stable implant in case of applications where no bone fracture has to be bridged.

In another embodiment the blade, comprises a coaxial bushing at its trailing end, said bushing having a central bore extending coaxial to the longitudinal axis and being apt for partially receiving the bone screw. The bushing may be configured as a rotational bearing for the bone screw such that the screw head of the bone screw may rotate within the central bore of the bushing and may be axially secured towards the blade by means of a contracted portion in the central bore.

In a further embodiment, the central bore is provided with an interior thread and the blocking means comprise a threaded fastener which is screwable into the interior thread of the bushing. This has the advantage that the screw head of the bone screw may be rotatively and axially fixed within the central bore simply by tightening the pre-assembled fastener. Furthermore the manufacture of the blocking means is very simple.

In a further embodiment, the bone screw comprises a screw head slideably fitting with a circular cylindrical portion of the central bore in the bushing. This has the advantage that the circular cylindrical portion acts as a rotational bearing for the screw head.

In a further embodiment the central bore, in the bushing comprises a contracted portion between the circular cylindrical portion and the blade such that a shoulder abutting the screw head is being formed. The advantage lies in the fact that the screw head may be clamped between the fastener and the shoulder.

In a further embodiment, the blade is provided with at least one cutting edge located on the terminal face of the leading end. By this the blade is self-cutting.

In a further embodiment, the blade is provided with two cutting edges intersecting at the longitudinal axis and enclosing an angle $\alpha<180°$. An improved cutting quality of the blade results by this arrangement.

In a further embodiment, the bushing is provided with a conical exterior lateral area which tapers towards that end of the bushing that is located opposite the blade. The conical configuration of the bushing permits an attachment of other instruments, tools or parts of the implant being used during implantation, reduction and/or the final fixation of the bone fragments.

Purposefully the blade, may have a thickness in the range of 0.2 mm to 3.0 mm, preferably in the range of 0.5 mm to 1.5 mm and a width measured transversely to its longitudinal axis in the range of 4 mm to 50 mm, preferably in the range of 10 mm to 25 mm.

In a further embodiment, the outer diameter of the thread is constant except for the region of the front end.

In a further embodiment, the shaft tapers from the rear end towards the front end, preferably in a conical manner. Preferably the shaft tapers with a cone angle in the range of 0.5° to 5°.

In a further embodiment, the blade is provided with one or more perforations which may have a diameter in the range of 0.5-3.0 mm. Preferably these perforations have a total area of less than 40% of the total surface area of said blade.

In a further embodiment, the shaft and the blade (7) are cannulated. The shaft has preferably a minimal diameter at its front portion of 1.0 mm and a maximum diameter at its rear portion of 15 mm. The depth of said thread has preferably a minimum value of 0.2 mm at said rear portion.

FIGS. 1 to 3 depict an embodiment of the osteosynthetic device comprising a bone screw 1 and a coaxially attached wing-like blade 7 having plane first and second surfaces 19,20 which are parallel and first and second lateral surfaces 31,32 being transverse to the first and second surfaces 19,20. Furthermore, the blade 7 is provided with an essentially rectangular coaxial aperture 17 which penetrates the blade 7 between the first and second surface 19,20. The aperture 17 being apt to receive the bone screw 1.

As shown in FIGS. 2 and 3, the bone screw 1 has a screw head 10 at the rear end 5 and adjacent a shaft 2 bearing a thread 3 with a core diameter tapering towards the front end 4 of the bone screw 1. Furthermore, the screw head 10 is provided with receiving means 12 apt for an engagement of a screw driving device, e.g. a hexagonal socket or a TORX (FIG. 3).

As shown in FIG. 2, the blade 7 is beveled at the terminal face of the leading end 8 and comprises two cutting edges 13 extending parallel to the first surface 19 of the blade 7 and intersecting on the longitudinal axis 6. The cutting edges 13 are mutually angled and intersect on the longitudinal axis 6 with an obtuse angle $\alpha$ of about 150°. At the leading end 8 of the blade 7 a coaxial cap 14 is fixedly inserted in the blade 7, whereby the cap 14 tapers towards a tip 16 which is terminally located on the longitudinal axis 6 and is in alignment with the cutting edges 13. Furthermore, the cap 14 is provided with a coaxial bore 29 being apt as a bearing for the front end 4 of the shaft 2. At the trailing end 9 of the blade 7 a bushing 18 is coaxially attached to the blade 7, said bushing 18 having an interior thread 22 arranged in the coaxial central bore 21 of the bushing 18. Furthermore, the blade 7 is provided with a plurality of perforations 11 which penetrate the blade 7 between the first and second surfaces 19,20.

FIGS. 2 and 3 show the blocking means 15, which is configured as a threaded fastener 23, and is screwable into the interior thread 22 in the central bore 21 of the bushing 18. The inner diameter d (d not shown) of the interior thread 22 is slightly greater than the outer diameter of the screw head 10 of the bone screw 1 such that the bone screw 1 may be mounted to the device through the central bore 21 of the bushing 18. Towards the blade 7 a circular cylindrical portion 24 of the central bore 21 coaxially adjoins the portion of the central bore 21 which is provided with the interior thread 22. This circular cylindrical portion 24 of the central bore 21 has a diameter D (D not shown) corresponding to the outer diameter of the screw head 10 such that the circular cylindrical portion 24 of the central bore 21 is apt as a rotational bearing for the bone screw 1. Furthermore, the central bore 21 is further provided with a contracted portion 26 having a smaller diameter than the circular cylindrical portion 24 of the central bore 21. Since the contracted portion 26 of the central bore 21 is arranged adjoining the circular cylindrical portion 24 towards the blade 7 a shoulder 25 is formed in the central bore 21 at the transition between the circular cylindrical portion 24 and the contracted portion 26. Upon tightening the fastener 23 the screw head 10 is pressed against the shoulder 25 in the central bore 21 such that the bone screw 1 is axially and rotatively fixed relative to the blade 7.

FIG. 3 illustrates how the fastener 23 is further provided with a through opening 27 being apt for the acceptance of a screw driver and having e.g. a hexagonal cross-section. The inner minimum width of the through opening 27 is slightly greater than the outer maximum width of the receiving means 12 being provided in the screw head 10 of the bone screw 1 such that the bone screw 1 may be screwed into a bone with the pre-assembled fastener 23. The exterior lateral area 28 of the bushing 18 is conically configured such that it tapers towards that end of the bushing 18 which is opposite the blade 7 therewith permitting an attachment of other instruments or tools.

Description of the Surgical Procedure a) Pre-drilling of a bore according to the planned engagement length of the bone screw 1 with a diameter equal to the diameter of the shaft 2 at the front end 4;
b) Introduction of the tip into said pre-drilled hole until the threads 3 of the bone screw 1 get in touch with the bone. The front portion of the blade 7 is manually pressed into the bone during this introduction phase;
c) Turning the bone screw 1 with light axial pressure will lead the threads 3 to find grip in the bone. When the bone screw 1 has found first grip, no further pressing is necessary and pure turning of the bone screw 1 will drive the screw and the blade 7 into the bone;
d) When the rear portion of the blade 7 gets in touch with the bone, turning shall be stopped and the device is in place;
e) Now the bone screw 1 and the blade 7 are blocked against each other by tightening the blocking mechanism.

The invention claimed is:

1. A fixation device for the fixation of a bone or bone fragments, the fixation device comprising:
a bone screw having a screw head and a screw end spaced apart from the bone screw head along a longitudinal direction, and an externally threaded shaft that extends from the bone screw head along the longitudinal direction, the bone screw head defining a maximum head cross-sectional dimension, and the externally threaded shaft defining a maximum threaded shaft cross-sectional dimension that is less than the maximum head cross-sectional dimension, the maximum head cross-sectional dimension and the maximum threaded shaft cross-sectional dimension each defined along a radial direction that is perpendicular to the longitudinal direction;
a blade having a leading end, a trailing end spaced apart from the leading end along the longitudinal direction, and an elongate aperture that extends between the trailing end of the blade and the leading end of the blade, the blade further defining opposing first and second planar surfaces that define a length along the longitudinal direction from the trailing end to the leading end and a width along a transverse direction that is perpendicular to the longitudinal direction, the first and second planar surfaces spaced apart by a thickness of the blade, the thickness perpendicular to the transverse direction and less than the length, the width, and the maximum head cross-sectional dimension; and
a bushing supported by the trailing end of the blade such that the blade extends from the bushing along the longitudinal direction, the bushing having a central bore sized and configured to receive at least a portion of the bone screw head therein,
wherein the bone screw head is disposed outside the elongate aperture and is rotatably coupled to the trailing end of the blade, the screw end is rotatably coupled to the leading end of the blade so that the bone screw is rotatably mounted with respect to the blade within the elongate aperture, and rotation of the bone screw with respect to the blade does not cause the bone screw to translate along the longitudinal direction with respect to the blade.

2. The fixation device of claim 1, further comprising a blocking device configured to be coupled to the bushing, such that the blocking device is movable relative to the trailing end of the blade between a first position whereby the blocking device blocks the rotation of the bone screw with respect to the blade, and a second position whereby the blocking device does not block the rotation of the bone screw with respect to the blade.

3. The fixation device of claim 2, wherein the blocking device is a threaded fastener, and rotation of the threaded fastener into the first position causes the bone screw head to press against a portion of the bushing so that the bone screw is rotationally fixed relative to the blade.

4. The fixation device of claim 3, wherein movement of the blocking device into the first position fixes the bone screw head in the central bore of the bushing against the portion of the bushing such that the bone screw is rotationally fixed relative to the blade.

5. The fixation device of claim 2, wherein the bushing defines a shoulder that is aligned with the bone screw head, wherein when the blocking device is in the first position, the bone screw head is captured between the blocking device and the shoulder.

6. The fixation device of claim 1, wherein the blade includes a bore that is distal to the elongate aperture along a distal direction toward the leading end of the blade, and the screw end of the bone screw includes a projection, the projection is at least partially received within the bore of the blade such that the screw end of the bone screw is rotatably coupled to the leading end of the blade.

7. The fixation device of claim 1, wherein the central bore of the bushing further includes a circular cylindrical portion, a reduced diameter portion spaced from the circular cylindrical portion in a distal direction toward the leading end of the blade, the reduced diameter portion having an internal diameter that is less than the maximum head cross-sectional dimension.

8. The fixation device of claim 1, wherein the central bore of the bushing extends along the longitudinal direction, the bushing further defining a shoulder that is aligned with the bone screw head along the longitudinal direction.

9. The fixation device of claim 1, wherein the bushing defines a conical exterior surface that tapers towards an end of the bushing that is located opposite the blade.

10. The fixation device of claim 1, wherein the leading end of the blade defines at least one cutting edge.

11. The fixation device of claim 10, wherein the at least one cutting edge is two cutting edges that intersect at a longitudinal axis, the two cutting edges defining an angle that is less than 180°, wherein the longitudinal axis is aligned with the longitudinal direction.

12. The fixation device of claim 1, wherein the first planar surface defines a first surface area, the blade further including a plurality of perforations, wherein the plurality of perforations define a second surface area, the second surface area being less than 40% of the first surface area.

13. The fixation device of claim 1, wherein the externally threaded shaft and the blade are cannulated.

\* \* \* \* \*